United States Patent [19]
Crane

[11] Patent Number: 5,900,248
[45] Date of Patent: May 4, 1999

[54] SYRINGEABLE ENTERAL DIET FOR ANIMALS IN A HYPERMETABOLIC STATE CAUSED BY THE STRESS OF MEDICAL AND SURGICAL ILLNESS

[75] Inventor: Stephan D. Crane, Topeka, Kans.

[73] Assignee: Colgate Palmolive Company, New York, N.Y.

[21] Appl. No.: 09/017,414

[22] Filed: Feb. 2, 1998

Related U.S. Application Data

[62] Division of application No. 08/051,492, Apr. 22, 1993, Pat. No. 5,714,161.

[51] Int. Cl.$^6$ .......................... A61K 47/26; A61K 47/42; A61K 47/44
[52] U.S. Cl. .......................... 424/439; 426/648; 514/937
[58] Field of Search .......................... 424/439; 426/648; 514/937

[56] References Cited

U.S. PATENT DOCUMENTS 5,221,668  6/1993  Henningfield et al. .................. 514/23

*Primary Examiner*—Carlos A. Azpuru
*Attorney, Agent, or Firm*—Paul Shapiro

[57] ABSTRACT

Disclosed herein is a nutrient composition suitable for enteral feeding of an animal in a state of metabolic stress. The composition is in the form of a suspension having a yield stress of about 1800 to about 5800 dynes/cm$^2$ wherein it is syringeable and capable of being administered to the animal directly through the oral cavity.

1 Claim, No Drawings

SYRINGEABLE ENTERAL DIET FOR ANIMALS IN A HYPERMETABOLIC STATE CAUSED BY THE STRESS OF MEDICAL AND SURGICAL ILLNESS

This is a divisional of prior application Ser. No. 08/051,492 filed Apr. 22, 1993 now U.S. Pat. No. 5,714,161.

BACKGROUND OF THE INVENTION

1. Field of the Invention

This invention relates to a nutritionally fortified enteral semi-viscous diet formulation for feeding to dogs, cats and other animals in state of metabolic distress and more particularly to an enteral diet which is in syringeable form and can be administered to the animal or pet directly through the oral cavity.

2. The Prior Art

Animals such as household pets such as dogs and cats suffering from an injury, illness or major surgery are highly susceptible to the post-stress development of anorexia and malnutrition.

The metabolic response to early, significant injury in an animal is represented by a shock phase which lasts about 48 hours and a late hypermetabolic phase which usually peaks at 72 to 96 hours after injury and subsides in days to weeks. The hypermetabolic state results from activation of general or local inflammatory response(s), and development of a sustained state of hypermetabolism and increased caloric expenditure. Suppression of the immune response, nutrient depletion of the plasma and tissue levels and sequential organ failure and death may result if the hypermetabolic state is allowed to persist without intervention. Other prominent tissue and biochemical responses to stress, injury and the hypermetabolic responses include loss of lean body mass, urinary nitrogen loss, hyperglycemia, carbohydrate intolerance, insulin resistance, glucosuria and gluconeogenesis. In a pet animal where the GI tract is still functioning, but the animal is unable to feed itself to take in adequate amounts of nutrients, enteral nutrition is of known benefit in practical therapeutics. The enteral route is the preferred route of nutritional administration relative to the parenteral route.

Enteral diets are sometimes administered to the pet animal in hypermetabolic and catabolic states through a feeding tube that may be used transiently with normal placement procedures or by a surgical placement of an indwelling tube. In the case of pet animals such as dogs and cats, the animals may find the tubing uncomfortable and may not cooperate with such feeding techniques. Hand feeding of the animal is difficult as the injured animal oftimes refuses to eat.

Therefore there is a need in the art for a ready-to-use enteral diet which may be readily administered by assisted feeding to hypermetabolic and catabolic animals which does not require a surgically implanted feeding tube or the intervention of a skilled professional or semi-professional.

SUMMARY OF THE INVENTION

In accordance with the present invention, to meet the nutritional needs of a hypermetabolic, nutritionally distressed pet animal patient which is unable to feed itself, refuses to eat, or otherwise requires assistance in feeding, there is provided a method of feeding an animal directly through the oral cavity which method includes injecting into the oral cavity of the pet animal, an enteral formulation fluid enough to be syringeable, the composition of the formulation being adjusted to present to the animal a specific distribution of proteins, carbohydrates and fats as well as essential amino acids, fatty acids, vitamins and trace elements in sufficient amounts and ratios to attenuate the hypermetabolic and catabolic responses associated with an injury, illness or surgery and to assist in restoration and repletion of body nutrients.

As the syringeable enteral diet of the present invention can be administered orally to animals by such administration there is avoided the need and cost for surgical implantation of a feeding tube to administer the diet formulation.

DESCRIPTION OF THE PREFERRED EMBODIMENTS

As used herein, the term "syringeable" means that the emulsified enteral composition is flowable through the tip of a syringe, the syringe having a capacity of 6 to 60 cc and a tip opening of about 2 to about 8 mm. Tip openings of this size are easily insertable into the mouth or between the teeth of a pet animal such as a dog or cat without imposing any substantial discomfort in the animal. By the use of such syringe administration, the enteral composition can be injected from such a syringe through the tip directly into the mouth of an animal without causing serious discomfort to the animal.

In practicing the method of the present invention, a feeding syringe of 6 to 60 cc capacity having a tip opening of 2 to 8 mm is filled with a syringeable emulsified suspension of an enteral diet and the tip of the syringe is inserted into the mouth of the animal. Upon insertion, the syringeable composition is delivered slowly and gently through the tip opening at a rate of about 5 to about 60 cc per minute. This rate allows the animal to swallow comfortably. When the syringe has been emptied, it is refilled and feeding of the enteral diet is continued in this manner until the animal has swallowed the desired quantity of the syringeable composition determined by food dose calculations relating to the animal's caloric requirements divided by the caloric density of the enteral formulation.

In the case of feeding a cat, in accordance with the method of the present invention, the syringe tip is inserted between the cat's upper and lower incisor teeth and the enteral diet is then delivered slowly, allowing the animal to swallow. In the case of a dog, the syringe tip is inserted between the cheek and the teeth of the animal.

The enteral diet composition used in the practice of the present invention is an emulsified aqueous suspension range having a yield stress value of about 1800 to about 5800 dynes/cm$^2$. At this yield stress value the suspension can be stored in ready-to-use form and is sufficiently viscous to physically suspend any insoluble ingredients present therein and yet be sufficiently fluid to be syringeable, that is, easily flowable and removable from a reservoir and dischargeable from a syringe tip.

The term "yield stress" as used in the present specification and claims means the yield stress of the emulsified enteral diet composition as measured by the vane method as reported by Dzuy et al in the Journal of Rheology 29(3), 335–347 (1985) the disclosure of this report being incorporated herein by reference. In the vane method a four-bladed vane is immersed in a concentrated suspension and rotated slowly at a constant rate to detect the yielding moment when the torque exerted on the vane shaft reaches a maximum value. Yield stress (ty) is calculated in accordance with the formula:

$$t_y = {}^{T}max/2^1 R^2 L$$

where $\tau_y$ = yield stress (dynes/cm²)

$T_{max}$ = torque maximum (dynes/cm) = 114,992 dyne-cm (value at 100% torque)(% torque)

R = Vane radius (1.235 cm)

L = Vane width (0.94 cm)

whereby $\tau_y$ = (% torque * 114,992)¹(1.524)²(0.94).

For yield stress values in the range of about 1800 to about 5800 dynes/cm² the maximum percent torque values range from about 15 to about 45.

At a yield stress value in the range of about 1800 to about 5800 dynes/cm² the emulsified suspension is in ready-to-use form and has a consistency between a liquid and a semi-solid resembling strained baby food. At a yield stress below about 1800 dynes/cm² the suspension is too fluid to be effectively administered and when it is attempted to administer such fluid product by syringe, the product is found to run out of the animal's mouth. At a yield stress substantially above about 5800 dynes/cm² the product is found to be difficult to be drawn into the syringe from a reservoir of product. At a yield stress between about 1800 and 5800 dynes/cm², the suspension can be readily drawn into the storage compartment of the syringe through its tip opening and is similarly dischargeable therefrom in a steady, controlled manner to allow for swallowing of the discharged suspension by the animal at a rate with which the animal is comfortable.

A syringeable enteral diet formulation which may be used in the practice of the present invention is a nutritionally fortified composition containing protein in an amount of about 5 to about 15% by weight, carbohydrate in an amount of about 2 to about 8% by weight, and fat about 4 to about 10% by weight.

To meet the needs of patients in the hypermetabolic state, the enteral diet is configured to have a metabolizable energy content of about 1.0 to about 1.5 kcal/g. Further the composition of the enteral diet is adjusted to emphasize essential amino acids, essential fatty acids, vitamins, minerals and trace elements. These substances are specifically included in the composition to meet the specific requirement needs of an animal in a hypermetabolic, catobolic state of nutritional distress.

In particular, the diet contains no less than about 10% protein derived from a high quality protein source such as liver, meat and casein, about 3 to about 5% carbohydrate derived from intact starches from corn flour and from about 5 to about 10% fat derived from animal adipose tissue and marine fish oils.

The formulation described here may also contain 100% or greater of the 1985 NRC requirements for minerals and vitamins, specifically, 0.10–0.30% phosphorous, 70–80 ppm iron, 50–60 ppm, zinc, 1.5–3.0 ppm, copper and Vitamin E, 80–90 IU/kg.

The composition may further include amino acids such as glutamine/glutamate 1.0–3.0%, by weight, arginine, 0.4 to 0.6% by weight and taurine 0.1–0.2% by weight as well as branched chain amino acids e.g. leucine, isoleucine, and valine, 1.5–2.0% by weight, as well as fatty acids, including n-3 fatty acids, 0.1 to 5.0% by weight.

The composition of the present invention is prepared as a ready-to-use composition by methods well known in the art including emulsification of the ingredients using high speed mixers and micropulverizers, the water content of the emulsified composition being in the range of about 65–85% by weight of the composition.

In preparing the enteral diet suspensions used in the practice of the present invention, the ingredients are added to water and the mixture mechanically worked to reduce the particle size of any suspended protein, fat and carbohydrate materials and to throughly dispense them in the aqueous suspension. The average particle size of the suspended materials being sufficiently small so that the suspension is syringeable through a syringe tip having an opening diameter of about 2 to 8 mm. Particle size reduction and dispersion can be accomplished with the use of a colloid mill, sonic mill, micropulverizer or other comparable equipment. The fluidity of the suspension is adjusted with water to obtain a syringeable composition having a yield stress of about 1800 to about 5800 dynes/cm². Up to 85% of the total emulsified suspension can be water.

The above disclosure generally describes the present invention. A more complete understanding can be obtained by reference to the following specific Example which is provided herein for purposes of illustration only and is not intended to be limiting.

EXAMPLE

The components listed on the Table below were combined using appropriate cooking and microemulsifying techniques in the amounts described below to produce a homogenous suspension having a metabolizable energy content of 1.20 kcal/g. The yield stress of the suspension was determined to be in the range of 1800 to 5800 dynes/cm².

TABLE

| Nutrient | Quantity, Wt % |
|---|---|
| Water | 77.00 |
| Protein | 10.50 |
| Fat | 6.60 |
| Carbohydrate | 4.00 |
| Potassium | 0.21 |
| Glutamine/Glutamate | 1.50 |
| Arginine | 0.51 |
| Taurine | 0.12 |
| Branched Chain Amino Acids | 1.93 |
| n-3 fatty acids (% of total fatty acids) | 4.32 |
| Vitamins and Trace Elements | ppm |
| Iron | 76.00 |
| Zinc | 54.00 |
| Copper | 2.10 |
| Vitamin E | 85.00 (IU/kg) |

The protein ingredient was derived from casein, chicken and liver. The fat ingredient was derived from mechanically deboned chicken and neuboden fish oil. The carbohydrate ingredient was derived from corn flour.

The enteral diet product had a consistency similar to a strained meat baby food. The enteral diet product flowed smoothly through a feeding syringe having a 5 mm tip.

Clinical Test

The composition of the Example was fed to dogs and cats which had injury, cancer, or infections that were treated by surgery, chemotherapeutic agents or both wherein the presence of a sustained hypermetabolic state was considered very likely.

The dogs were fed using a 35 or 60 cc syringe having a 5 mm tip opening wherein the syringe tip was inserted in the dog's mouth between the cheek and gum and the formula slowly delivered, at a rate of about 20 cc/minute allowing the pet to swallow comfortably when the syringe was emptied. The syringe was refilled and feeding continued until the dog had swallowed the calculated quantity or an amount deemed adequate by the attending veterinarian.

Cats were fed in a similar manner except the tip was inserted between the cat's upper and lower small front teeth and the rate of delivery was reduced.

A high percentage of the animals fed in this manner responded positively to the feeding technique, many, gaining weight during the therapeutic program despite the seriousness of their primary illnesses, indicating that such nutritional intervention during the distress of anoreria, hypermetabolism and catobolism can lead to a positive clinical outcome.

What is claimed is:

1. A composition for feeding a household pet in a state of metabolic distress which composition comprises an enteral diet formulation having a yield stress of about 1800 to about 5800 $cm^2$ which is flowable through a syringe tip having an opening diameter of 2 to 8 mm whereby the composition is administered to the pet directly through the oral cavity.

* * * * *